United States Patent
Shaker et al.

(10) Patent No.: US 11,911,627 B1
(45) Date of Patent: Feb. 27, 2024

(54) METHOD OF USING A MEDICAL DEVICE

(71) Applicant: ALTRIX MEDICAL, INC., Centreville, VA (US)

(72) Inventors: Matthew Robert Shaker, Centreville, VA (US); Jesse S. Kruska, Westport, CT (US); Daniel Fleck, Potomac, MD (US)

(73) Assignee: Altrix Medical, Inc., Centreville, VA (US)

( * ) Notice: Subject to any disclaimer, the term of this patent is extended or adjusted under 35 U.S.C. 154(b) by 0 days.

(21) Appl. No.: 18/343,994

(22) Filed: Jun. 29, 2023

(51) Int. Cl.
*A61N 1/39* (2006.01)
*A61B 5/349* (2021.01)

(52) U.S. Cl.
CPC ............ *A61N 1/3904* (2017.08); *A61B 5/349* (2021.01); *A61N 1/3968* (2013.01); *A61N 1/3993* (2013.01)

(58) Field of Classification Search
CPC .... A61N 1/3904; A61N 1/349; A61N 1/3968; A61N 1/3993
See application file for complete search history.

(56) References Cited

U.S. PATENT DOCUMENTS

| | | | | |
|---|---|---|---|---|
| 5,645,571 A * | 7/1997 | Olson | ................... | A61N 1/3931 607/142 |
| 6,350,160 B1 | 2/2002 | Feuersanger | | |
| 8,798,743 B1 * | 8/2014 | Khuon | ................... | A61B 5/053 607/5 |
| 9,089,685 B2 | 7/2015 | Sullivan et al. | | |
| 10,799,709 B2 * | 10/2020 | Teber | ................... | A61N 1/3968 |
| 10,946,209 B2 | 3/2021 | Andrews et al. | | |
| 10,953,234 B2 * | 3/2021 | Kumar | ................... | A61N 1/025 |
| 11,185,709 B2 * | 11/2021 | Kumar | ................... | G16H 50/20 |
| 11,253,715 B2 * | 2/2022 | Kumar | ................... | A61B 5/282 |
| 11,433,249 B1 * | 9/2022 | Shaker | ................ | A61N 1/0492 |
| 11,547,863 B1 * | 1/2023 | Shaker | ................ | A61N 1/3904 |
| 11,633,613 B1 * | 4/2023 | Shaker | ................ | A61N 1/3904 607/5 |
| 2002/0156506 A1 * | 10/2002 | Kroll | ................... | A61N 1/3975 607/5 |
| 2004/0260376 A1 * | 12/2004 | Craige, III | ............ | A61N 1/046 600/382 |
| 2008/0033495 A1 * | 2/2008 | Kumar | ................ | A61N 1/3968 607/5 |

(Continued)

FOREIGN PATENT DOCUMENTS

EP 1372784 B1 5/2010

Primary Examiner — Eric D. Bertram
(74) Attorney, Agent, or Firm — Louis Ventre, Jr.

(57) ABSTRACT

A method of using a medical device to take multiple electrocardiograms (ECG) and, if needed, to be converted into an automated external defibrillator (AED). The medical device is configured to take the ECG without deploying any AED electrode pad and, if convenient, to be held by a person so that the person can simply put fingers from both hands on two contacts to take the ECG. Alternatively, the two contacts may be placed on the person's bare skin. The medical device is configured to separate into two components: An AED body and a cartridge. A computer for viewing the ECG may be built into the medical device or may be connected to the medical device. Conversion of the medical device to an AED occurs by removing a first AED electrode pad and a second AED electrode pad from a flattened and stacked arrangement within the cartridge.

8 Claims, 13 Drawing Sheets

(56) References Cited

U.S. PATENT DOCUMENTS

| | | | |
|---|---|---|---|
| 2009/0182241 A1 | 7/2009 | Maruccio | |
| 2011/0077497 A1* | 3/2011 | Oster | A61B 5/259 |
| | | | 600/300 |
| 2011/0257695 A1* | 10/2011 | Jonsen | A61B 50/31 |
| | | | 206/718 |
| 2014/0317914 A1* | 10/2014 | Shaker | A61N 1/046 |
| | | | 29/825 |
| 2015/0045869 A1* | 2/2015 | Albright | A61N 1/0492 |
| | | | 29/877 |
| 2015/0046175 A1* | 2/2015 | Jorgenson | A61N 1/3925 |
| | | | 705/2 |
| 2015/0073285 A1* | 3/2015 | Albert | H04B 5/0031 |
| | | | 600/509 |
| 2015/0273226 A1* | 10/2015 | Einy | A61N 1/3968 |
| | | | 607/6 |
| 2016/0045753 A1* | 2/2016 | Axness | A61N 1/3931 |
| | | | 607/5 |
| 2016/0095529 A1* | 4/2016 | Khuon | A61B 5/113 |
| | | | 600/509 |
| 2017/0056682 A1* | 3/2017 | Kumar | G16H 20/30 |
| 2017/0296804 A1* | 10/2017 | Kanemoto | A61N 1/0492 |
| 2019/0008409 A1* | 1/2019 | Kantor | A61K 9/703 |
| 2019/0022400 A1* | 1/2019 | Kumar | A61B 5/259 |
| 2019/0282821 A1* | 9/2019 | Masuda | A61B 5/282 |
| 2020/0094044 A1* | 3/2020 | Andrews | A61B 90/98 |
| 2020/0222707 A1* | 7/2020 | Kumar | A61N 1/046 |
| 2020/0282225 A1* | 9/2020 | Kumar | A61N 1/046 |
| 2021/0213296 A1* | 7/2021 | Kumar | A61B 5/4818 |
| 2022/0134121 A1* | 5/2022 | Kumar | A61N 1/3975 |
| | | | 607/7 |

* cited by examiner

METHOD OF USING A MEDICAL DEVICE

TECHNICAL FIELD

In the field of surgery, a method of using a device for medical evaluation of a condition of a living body, the method involving the detection of heartbeat electric signals and cardiovascular characteristics. Also, in the field of light, thermal, and electrical application, a device for applying electrical energy to the external surface and inside portions of the body to restore normal operation of the heart.

BACKGROUND ART

An electrocardiogram, often called an ECG or EKG for short, is a medical test performed to measure electrical activity of a person's heart. The medical test helps emergency medical technicians, doctors, and other medical professionals to understand how that person's heart is performing. In the case of potential cardiac emergencies, ECGs are also used to determine whether to treat the person with an electrical shock from a defibrillator (i.e., if the person has an abnormal cardiac rhythm that is considered treatable with defibrillation).

When the person's heart beats, it creates electrical signals that make the heart pump blood. These electrical signals can be detected and recorded by placing at least two sensors, called electrodes, on the person's skin, or commonly on the person's fingers, chest, arms or legs. These electrodes are connected to a device that picks up the electrical signals and translates them into a graph or a series of waves.

The graph produced by an ECG provides valuable information about the person's heart rate and rhythm, and can show whether there are any electrical abnormalities present. By analyzing the graph waveforms, medical professionals can often diagnose various heart conditions like arrhythmias (irregular heartbeats), heart attacks, and other heart diseases.

An ECG can be performed in a few seconds, and the results can be reviewed immediately by a healthcare professional. In the case of a cardiac emergency, output from an ECG is used to determine whether or not a defibrillator should be used on the person.

An automated external defibrillator (AED), is a device designed to be used by a non-medically trained person to help someone who is experiencing a sudden cardiac arrest. It is designed to deliver an electric shock to the heart in order to restore its normal rhythm. A sudden cardiac arrest occurs when the heart's electrical system malfunctions. Such arrythmias cause the heart to stop pumping blood effectively. AEDs are designed to provide a shock by using an ECG to detect if a shockable arrythmia is present.

When someone collapses due to a cardiac arrest, someone nearby can quickly utilize an AED to help them. AEDs are often found in public places like schools, airports, or shopping centers. The AED typically has a set of electrode pads with adhesive on one side of each. These pads preferably comply with requirements as specified for AEDs in "Medical electrical equipment—Part 2-4: Particular requirements for the basic safety and essential performance of cardiac defibrillators," International Electrotechnical Commission (IEC) standard 60601.2.4.

The rescuer typically removes the person's upper body clothing or items that might interfere with an AED electrode pad's contact with the person's chest. The AED electrode pads are placed on the person's bare skin, typically one on the upper right chest and the other on the middle-left side.

Once the AED electrode pads are in place, the AED automatically analyzes the person's heart rhythm to determine if an electric shock may help the person. If the AED detects a specific abnormal rhythm (i.e., ventricular fibrillation or ventricular tachycardia), it will usually prompt the rescuer to deliver an electrical shock by pressing a button (or in the case of fully automated AEDs, deliver that shock automatically). The electrical shock delivered by the AED may successfully renormalize the heart's electrical activity.

After the shock, the AED will continue to analyze the person's heart rhythm and provide guidance on whether additional shocks are necessary and may also provide guidance on the delivery of CPR (cardiopulmonary resuscitation).

SUMMARY OF INVENTION

A method of using a medical device configured to take multiple electrocardiograms (ECG) on one or more persons. The medical device is further configured to be converted into an automated external defibrillator (AED) when needed. The medical device is further configured to take the ECG without deploying any AED electrode pad and, if convenient, to be held by a person so that the person can simply put fingers from both hands on two contacts to take the ECG. Alternatively, the two contacts may be placed on the person's bare skin. The medical device is configured to separate into two components: An AED body and a cartridge. One or more computers for viewing and processing the ECG may be built into the medical device, may be connected to the medical device, or may be both built into the medical device and connected to the medical device.

Conversion of the medical device to an AED occurs by removing a first AED electrode pad and a second AED electrode pad from a flattened and stacked arrangement within the cartridge. The method then provides for attaching the first AED electrode pad and the second AED electrode pad to a person to be treated with the AED. Finally, the AED is activated to cause a defibrillating electrical shock to be administered through the AED electrode pads to the person.

The medical device may be used for multiple ECGs before conversion to an AED. When desired, the AED may be employed by separating the medical device into the cartridge and AED body, replacing the cartridge by plugging it into the AED body to enable the AED to supply an electrical shock to the person, pulling a rear cover off of the cartridge to reveal the AED electrode pads for placement on the person needing defibrillation, and activating the AED to send the electrical shock between the AED electrode pads.

Technical Problem

An AED would be significantly improved if it were reusable to take as many ECG measurements as desired without deploying the AED electrode pads.

An AED is not currently able to take an ECG without deploying the AED electrode pads.

After deployment of the AED electrode pads, the AED either must be serviced with replacement pads or discarded, which is wasteful when an ECG shows defibrillation is not necessary. Research has shown that reasons people do not use an AED include lack of confidence and fear of harming the person in distress. This invention allows a quick and unobtrusive way determine if use of the AED is necessary and, if such a determination is made, the provision of explicit coaching and prompts to coach a hesitant person into providing the required defibrillation.

Typical AEDs are not configured to report an ECG in real-time outside of a cardiac emergency. However, many patients need to report cardiac information routinely to a physician. Currently this non-emergency ECG collection requires a second device.

Solution to Problem

The solution is a medical device able to repetitively take an ECG from one or more persons, but quickly transform into a usable AED when needed. The medical device would compactly store the AED electrode pads within the medical device disconnected from an electricity source when in storage.

In the simplest process, conversion of the medical device from ECG capability to a functioning AED would be accomplished by performing two steps, and additional steps may be performed in any order that enables AED functionality: A first step of freeing the AED electrode pads from storage within the cartridge. And, a second step of applying the AED electrode pads on a person requiring defibrillation.

An optional third step of separating the medical device into two component parts: a cartridge and an AED body. At this point, the cartridge, which contains the pads, is now physically separated from the AED body. The AED electrode pads are not connected and cannot receive electricity. When the cartridge is separated from the AED body, then a fourth step is plugging the pins extending from the cartridge into the receptacles on the AED body, making the AED operating mode available for selection and use.

An optional fifth step of electrically isolating a first electrical contact and a second electrical contact for the ECGs from the source of electricity. This may be done automatically or manually, for example, to select AED operational mode.

Advantageous Effects of Invention

The method of using the medical device enables taking of multiple ECGs without deploying the AED electrode pads.

The method enables on-demand ECGs and associated transmission of ECG data during non-cardiac emergencies.

With simple reconfiguration steps, the method enables transformation of the medical device configured for repetitive ECG measurements into a functional AED.

The method enables compact storage of two AED electrode pads that are electrically disconnected from a source of electricity.

The method has a unique circuit board configuration with two CPUs that supports a compact design for both the ECG and AED functions.

BRIEF DESCRIPTION OF DRAWINGS

The drawings illustrate preferred embodiments of a method of using a medical device according to the disclosure. The reference numbers in the drawings are used consistently throughout. New reference numbers in FIG. 2 are given the 200 series numbers. Similarly, new reference numbers in each succeeding drawing are given a corresponding series number beginning with the figure number.

DESCRIPTION OF EMBODIMENTS

In the following description, reference is made to the accompanying drawings, which form a part hereof and which illustrate mandatory and optional steps of the method of using a medical device and also illustrate the components needed to implement these steps. The drawings and the preferred embodiments of the invention are presented with the understanding that the present invention is susceptible of embodiments in many different forms and, therefore, other embodiments may be utilized and structural, and operational changes may be made, without departing from the scope of the methodology disclosed.

Figure 1:
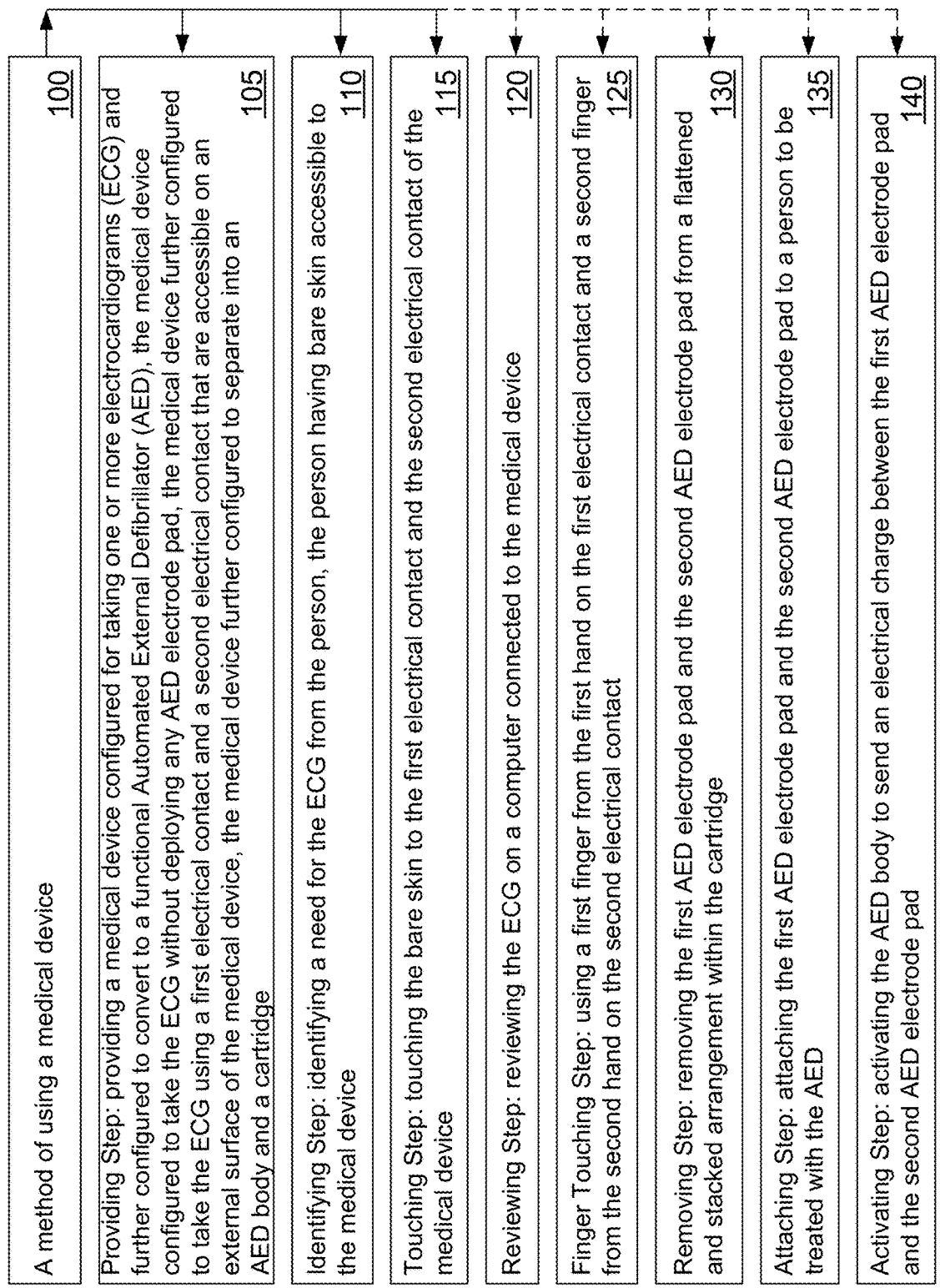
FIG. 1 is a chart of preferred mandatory steps and optional steps in the method of using the medical device. Mandatory steps are shown connected by a solid line and optional steps are shown connected by a dashed line.
Figure 2:
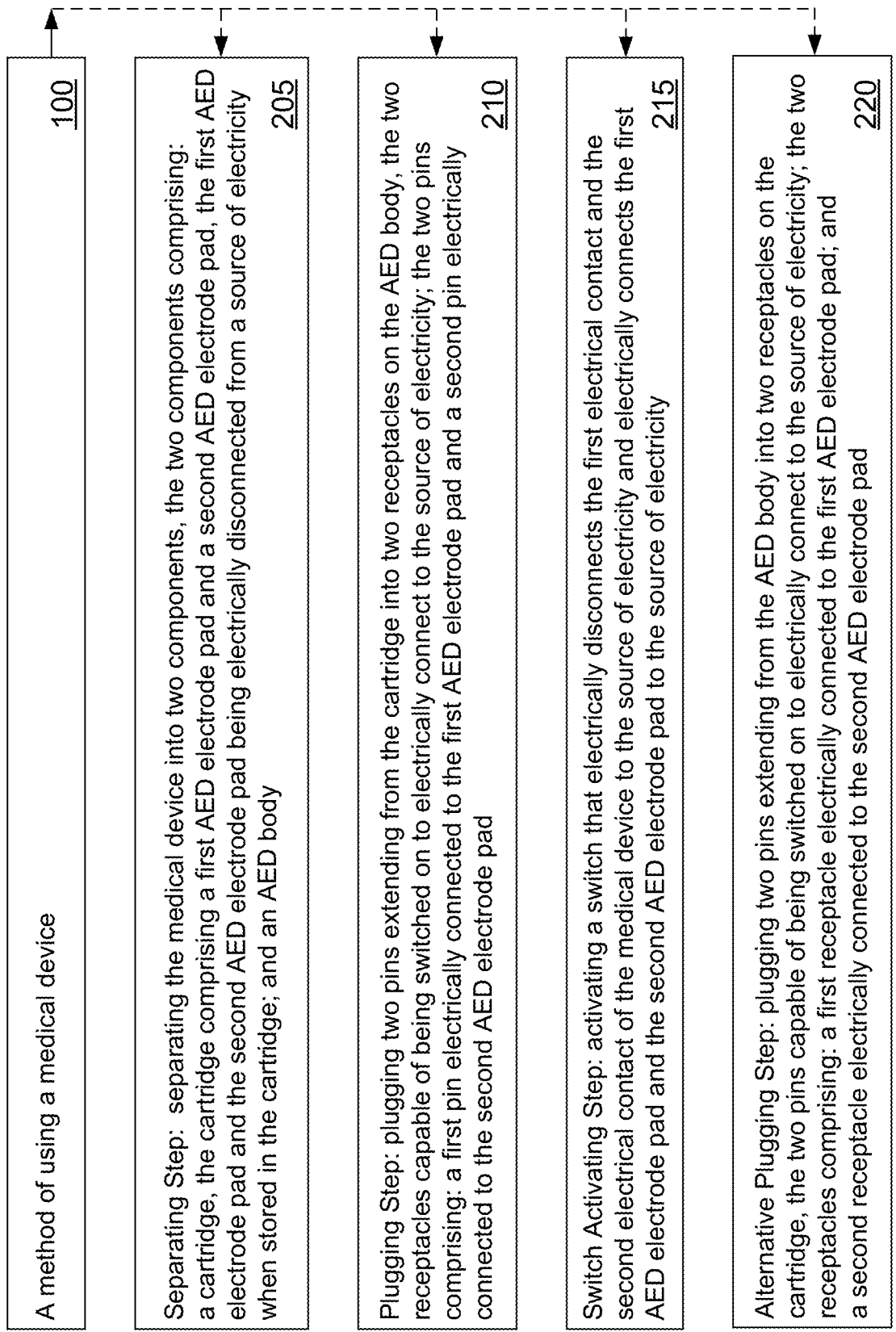
FIG. 2 is a continuation of the chart in FIG. 1 showing additional optional steps in the method of using the medical device.

Reference is made to FIG. 1 and FIG. 2, which chart the preferred mandatory steps and the preferred optional steps in a preferred method of using the medical device (300). The preferred steps are connected by solid lines and the optional steps are connected by dashed lines.

This disclosure relates to a method (100) of using a medical device (300), which may be used repetitively for taking an electrocardiogram, ECG (1325), from one or more persons. When desired, this medical device (300) can quickly and easily be converted to an automated external defibrillator, AED (900), capable of delivering an electrical shock (915) to a person (905) requiring defibrillation.

The medical device (300) is a combination tool that can function to take multiple ECGs without deploying any of the AED electrode pads, and then be converted to a functional AED, when needed.

Figure 9:
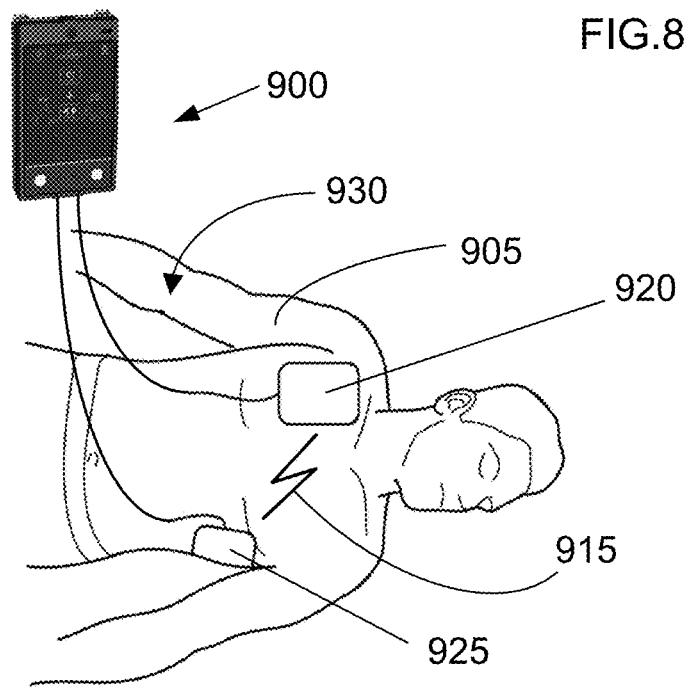
FIG. 9 is a top view of a person showing a typical placement of the AED electrode pads when the medical device has been transformed to function as an AED.
Figure 10:
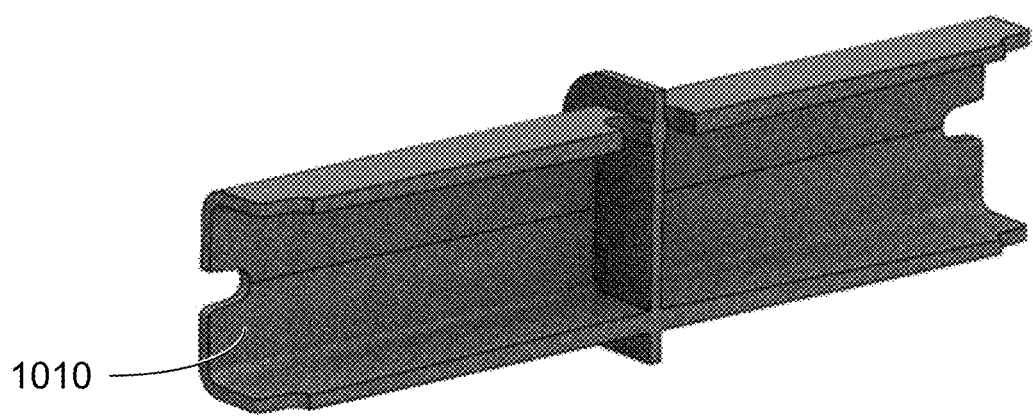
FIG. 10 is a lengthwise, sectional-perspective view showing half of a spool: the whole spool is used to store and hold the coiled wires connecting to the AED electrode pads.
Figure 11:
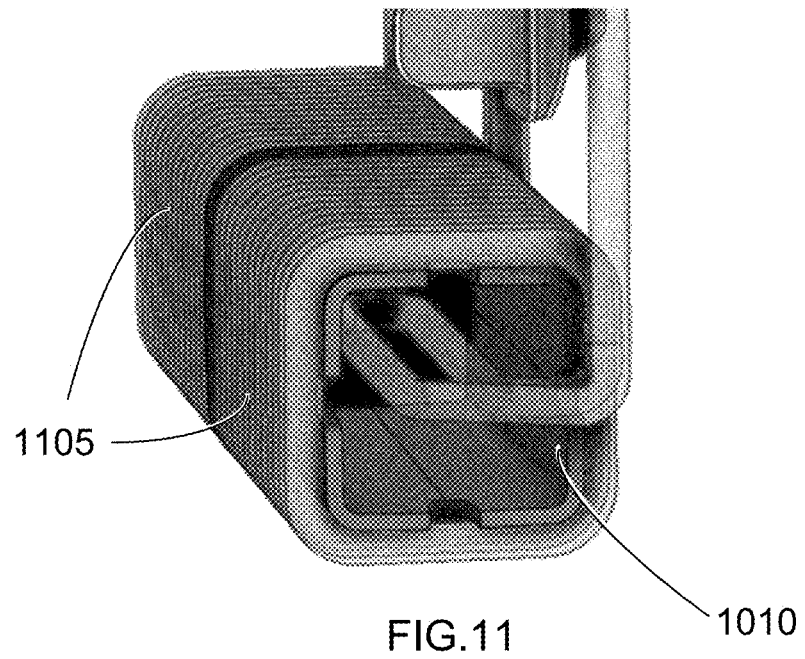
FIG. 11 is side perspective view of the coiled wires wrapped around the spool for storage.
Figure 13:
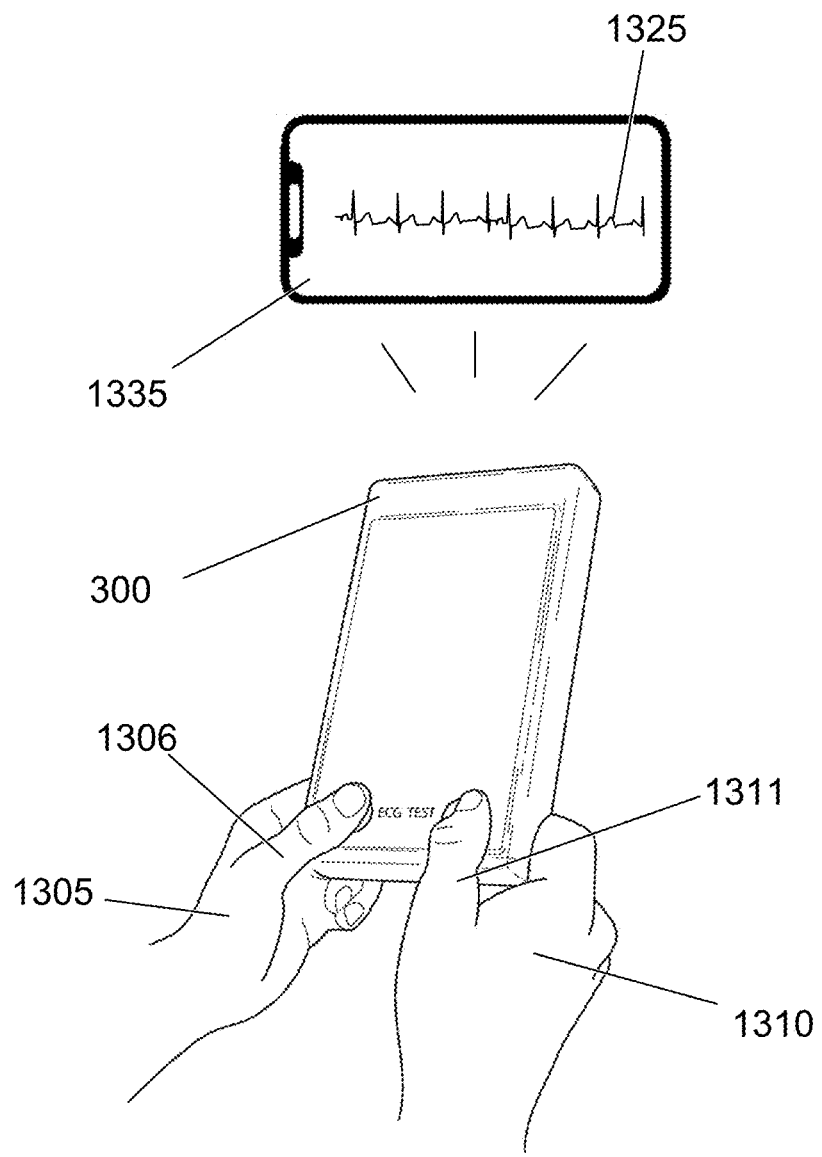
FIG. 13 is a perspective view the medical device showing a person's hands with thumbs on the first electrical contact and the second electrical contact to take the ECG displayed on a computer wirelessly connected to the medical device.

The medical device (300) has important inherent operational configurations. Referring to FIG. 13 for its use in taking an ECG (1325), the medical device (300) is configured for taking one or more electrocardiograms (ECG). Referring to FIG. 9 for its use as an AED (900), the medical device (300) is further configured to be converted by a user to function as the AED (900) to supply an electrical shock (915) to a patient or other person (905) requiring defibrillation.

The medical device (300) is configured to be held by a person (905) when taking an electrocardiogram, ECG (1325), or alternatively to be placed on bare skin (930) of the person (905). The medical device (300) is further configured to take an ECG (1325) from the person (905) without deploying any AED electrode pad, and that is by using a first electrical contact (305) and a second electrical contact (310), which are accessible on an external surface (315) of the medical device (300). The medical device (300) is furthered configured to separate into two components: an AED body (320) and a cartridge (325).

In an example of the use of an alternate implementation, the first electrical contact (305) and the second electrical contact (310) are placed on bare skin (930) of the person. In this example, the first electrical contact (305) is connected to the external surface (315) of the medical device (300) by a first electrically-conducting wire and the second electrical contact (310) is connected to the external surface (315) of the medical device (300) by a second electrically-conducting wire.

The cartridge (325) may be separated in the process of using the medical device (300) and for replacement of disposable AED electrode pads after they are used, or after the cartridge (325) is opened, or after the AED electrode pads are recommended for replacement. The cartridge (325) may be a rigid or non-rigid component. However, the cartridge (325) must comprise the AED electrode pads and be able to attach to the AED body (320) to form a functional AED (900).

The Method (100) of using the medical device (300) preferably includes a Providing Step (105), an Identifying Step (110) and a Touching Step (115). Optionally, the method (100) may include, a Reviewing Step (120); a Finger Touching Step (125); a Removing Step (130); a Separating Step (205); an Attaching Step (135); a Plugging Step (210); an Alternative Plugging Step (220); an Activating Step (140); and a Switch Activating Step (215).

The Providing Step (105) is providing a medical device (300) configured for taking one or more electrocardiograms, ECG (1325), without deploying any AED electrode pad. While there may be more than two such AED electrode pads in storage in the cartridge (325) that are capable of being deployed, when only two AED electrode pads are present in a preferred embodiment, then the limitation "without deploying any AED electrode pad" means that the ECG (1325) capability is present without deploying the first AED electrode pad (920) or the second AED electrode pad (925) stored within the cartridge (325).

The Providing Step (105) further specifies that the medical device (300) is further configured to be converted into a functional Automated External Defibrillator, namely the AED (900).

The ECG (1325) may be taken repetitively on one person or on multiple persons using a first electrical contact (305) and a second electrical contact (310), which are accessible on an external surface (315) of the medical device (300). More than two such electrical contacts may be present on the external surface (315) in alternative embodiments of the medical device (300).

Before conversion to an AED (900), the AED electrode pads are not used for taking the ECG (1325). The electrical contacts may be reused for ECG (1325) purposes as many times as is desired on as many persons as needing this diagnostic measurement without requiring replacement of the AED electrode pads.

Figure 3:
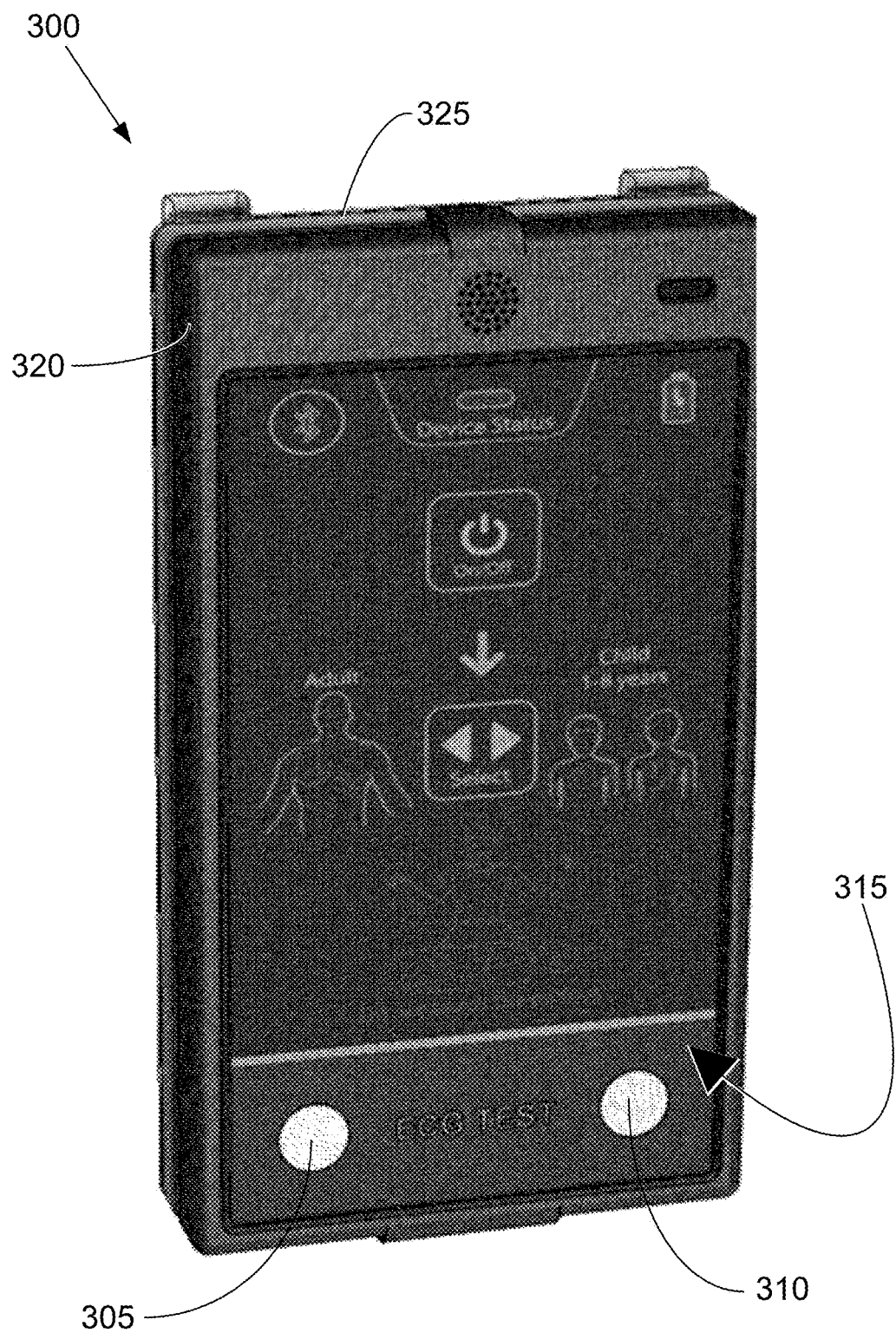
FIG. 3 is a front perspective view of the medical device uniting a cartridge at the rear and an AED body at the front.
Figure 4:
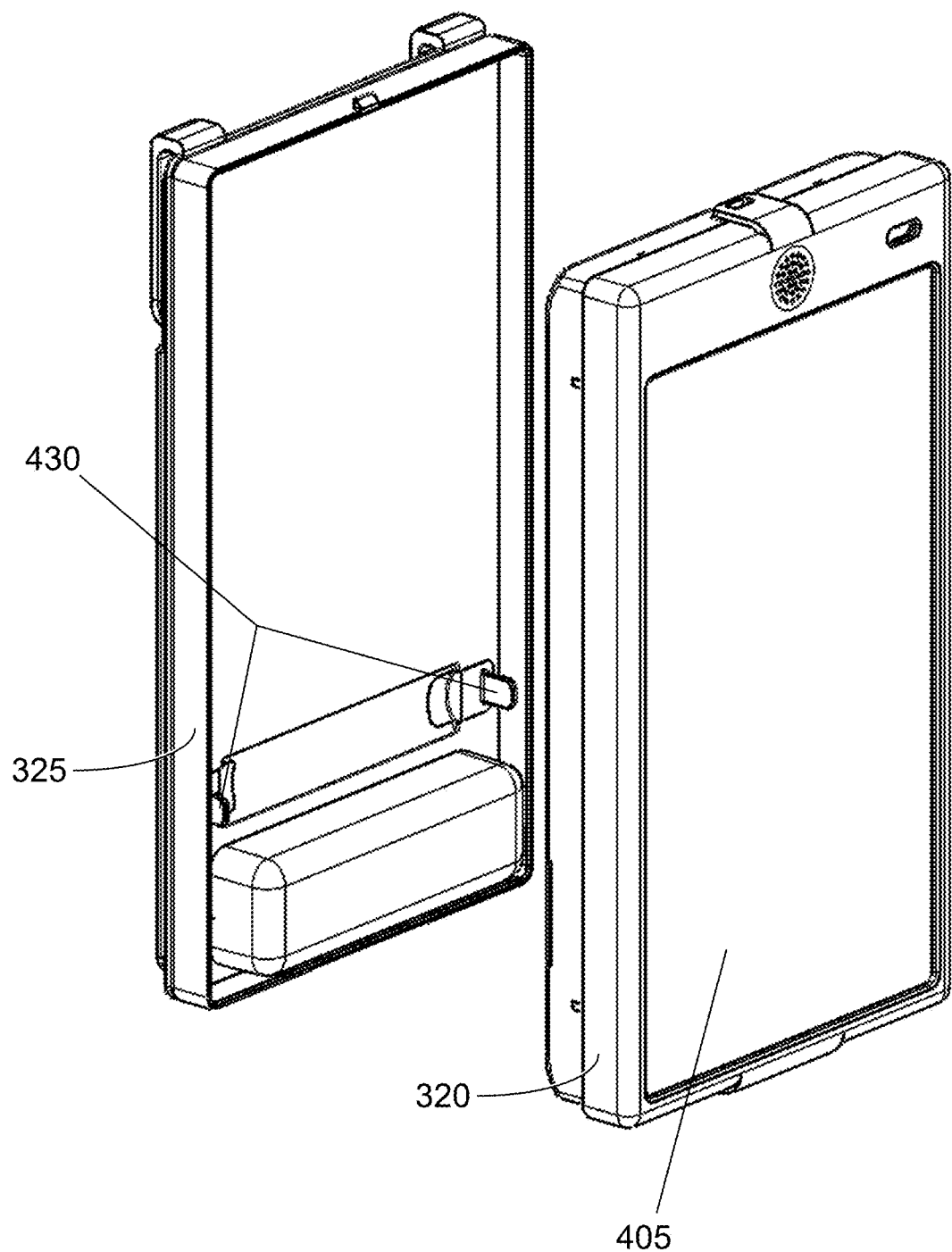
FIG. 4 is an exploded view of the medical device showing pins extending from the cartridge and ready for insertion into receptacles on the AED body.
Figure 5:
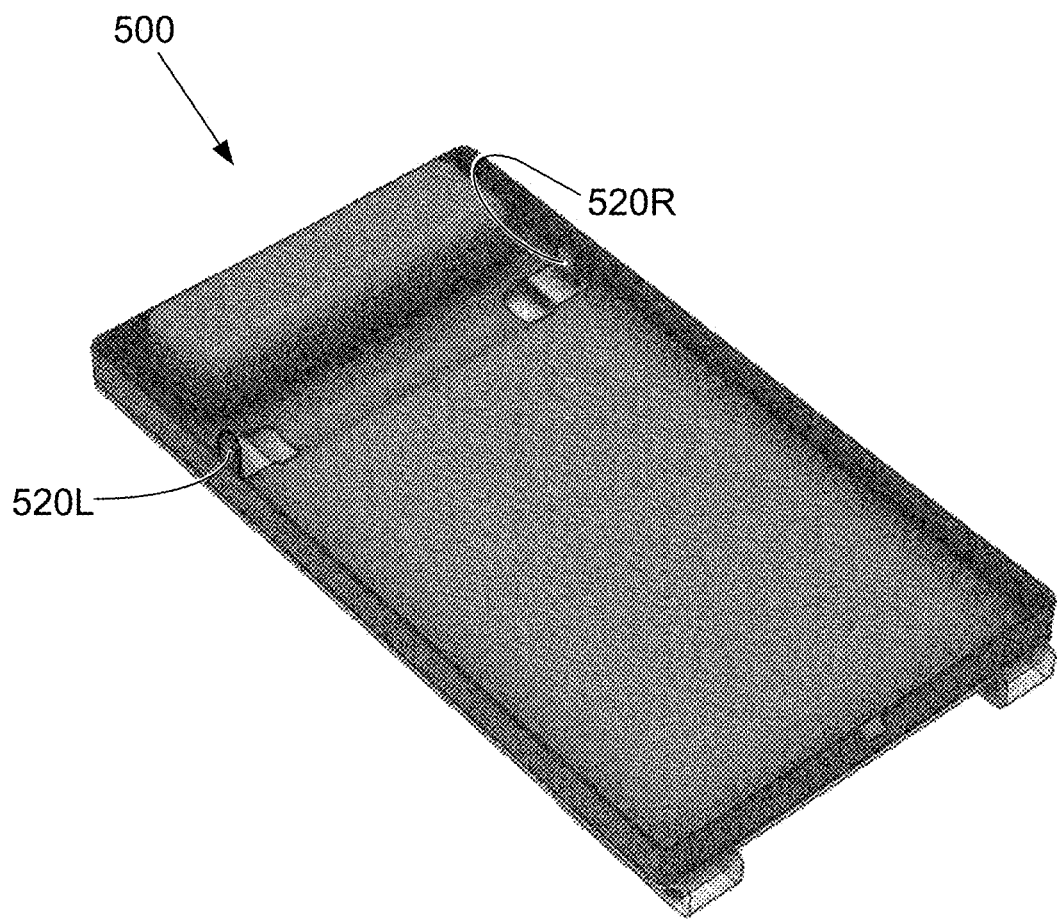
FIG. 5 is an internal view of the cartridge showing the pins available to connect electrode pads to receptacles in the AED body.
Figure 6:
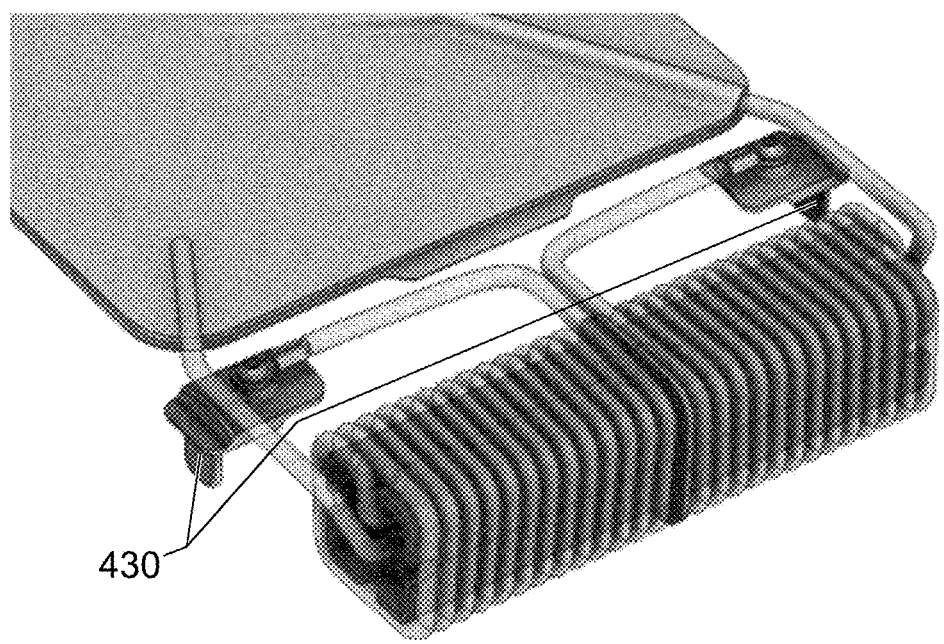
FIG. 6 is a partial perspective of stacked AED electrode pads connected to coiled wires that would be stored on a spool within the cartridge.

The Providing Step (105) further specifies that the medical device (300) is further configured to separate into two components. These two components are a cartridge (325) and an AED body (320), as shown in FIG. 3 and FIG. 4. The cartridge (325) may be replaced by a new cartridge after use of the AED electrode pads stored therein. The AED electrode pads typically have a sticky side for adhering to the skin of a person (905). After use on the person (905), the AED electrode pads could be used again, but would preferably be discarded with the cartridge (325) and a new replacement cartridge with two pins (430) and new AED electrode pads stored therein, would be attached to the AED body (320) to restore like-new capability to the AED (900).

The ECG (1325) may be taken by the AED body (320) both before and after separation of the medical device (300) into its two components, but, preferably, only so long as the first AED electrode pad (920) and the second AED electrode pad (925) remain disconnected from the electricity supply, to wit, the battery (1410) and/or the capacitor (1425). In order to retain ECG capability before and after separation, the first electrical contact (305) and a second electrical contact (310) remain accessible on the external surface (315) of the medical device (300) and are available to take an ECG (1325) both before and after any separation of the medical device (300) into the cartridge (325) and the AED body (320).

The Identifying Step (110) is identifying a need for the ECG (1325) from the person (905). The person (905) preferably has bare skin (930) accessible to the first electrical contact (305) and the second electrical contact (310) on the external surface (315) of the medical device (300). The bare skin (930) is preferably a finger from each hand, but may simply be exposed skin on the chest, arm, leg or other location on the person (905).

The Touching Step (115) is touching the bare skin (930) to the first electrical contact (305) and the second electrical contact (310) of the medical device (300). This Touching Step (115) involves placing the first electrical contact (305) and the second electrical contact (310) on the person's bare skin, which is sufficient for the electrical contacts to sense the electric heart signals and enable the medical device (300) to display the ECG on the computer (335).

As shown in FIG. 13, preferably, the bare skin (930) of the person (905) is found on the person's thumbs so that all the person need do is hold the medical device (300) in their hand or hands and place a thumb or other finger from each hand on the first electrical contact (305) and the second electrical contact (310). Thus, it is preferable that the person (905) has a first hand (1305) with one or more fingers and has a second hand (1310) with one or more fingers, and wherein the Touching Step (115) is accomplished by the person (905) using a first finger (1306) from the first hand (1305) on the first electrical contact (305) and a second finger (1311) from the second hand (1310) on the second electrical contact (310).

The Reviewing Step (120) is reviewing or examining the ECG (1325) on the computer (405) that is either within the medical device (300), as shown in FIG. 4, or is electronically connected to the medical device (300), as shown in FIG. 13. The computer (405) may be hard wired into the AED body (320), as indicated in FIG. 4; or the computer (405) may be a separate computing device, with a wired or wireless connection. For example, the separate computer may be a smartphone (1335), tablet, or laptop having a wireless connection, as indicated in FIG. 13.

When a defibrillation task is needed, the medical device (300) is converted into an AED (900) that is functional or operable. Such conversion begins by removing the AED electrode pads from the cartridge (325).

The Removing Step (130) is removing the first AED electrode pad (920) and the second AED electrode pad (925) from a flattened and stacked arrangement within the cartridge (325). These two AED electrode pads would preferably start out being disconnected or electrically isolated from an electricity source so that their storage within the cartridge (325) would provide no opportunity for unintended discharge.

When the AED electrode pads are connected to a source of electricity, the first electrical contact (305) and the second electrical contact (310) (aka, the finger electrodes) used for taking the ECG are automatically or manually disconnected from the source of electricity. Connecting the AED electrode pads to a source of electricity and disconnecting the first electrical contact (305) and the second electrical contact (310) from the source of electricity is preferably accomplished using a dual set of relays or a single pair of dual-pole relays. The relays would electrically isolate the finger electrodes and electrically connect the AED electrode pads to the electricity supply through internal circuitry. In an alternative implementation, the first electrical contact (305) and the second electrical contact (310) use a second source of electricity that is exclusively dedicated for ECG use.

Automatic electrical isolation of the ECG circuit and electrical activation of the AED circuit ensures that no electrical energy can be transmitted to the finger electrodes during usage of the device's AED functionality. Isolation of the finger electrodes would preferably meet the same energy withstand requirements as specified for AEDs in "Medical electrical equipment—Part 2-4: Particular requirements for the basic safety and essential performance of cardiac defibrillators," International Electrotechnical Commission (IEC) standard 60601.2.4. This standard requires that the insulation resistance of the device to withstand 1.5 times the highest peak working voltage.

A temporary electrical connection between the stored AED electrode pads may be implemented, if it were desired to test the AED electrode pads and the electrical discharge circuit. A possible method for such testing can be adapted using a liner and defined hole therein as a testing means described in applicant's earlier patent application, U.S. application Ser. No. 18/077,068, filed 7 Dec. 2022, which is hereby incorporated by reference herein.

Figure 12:
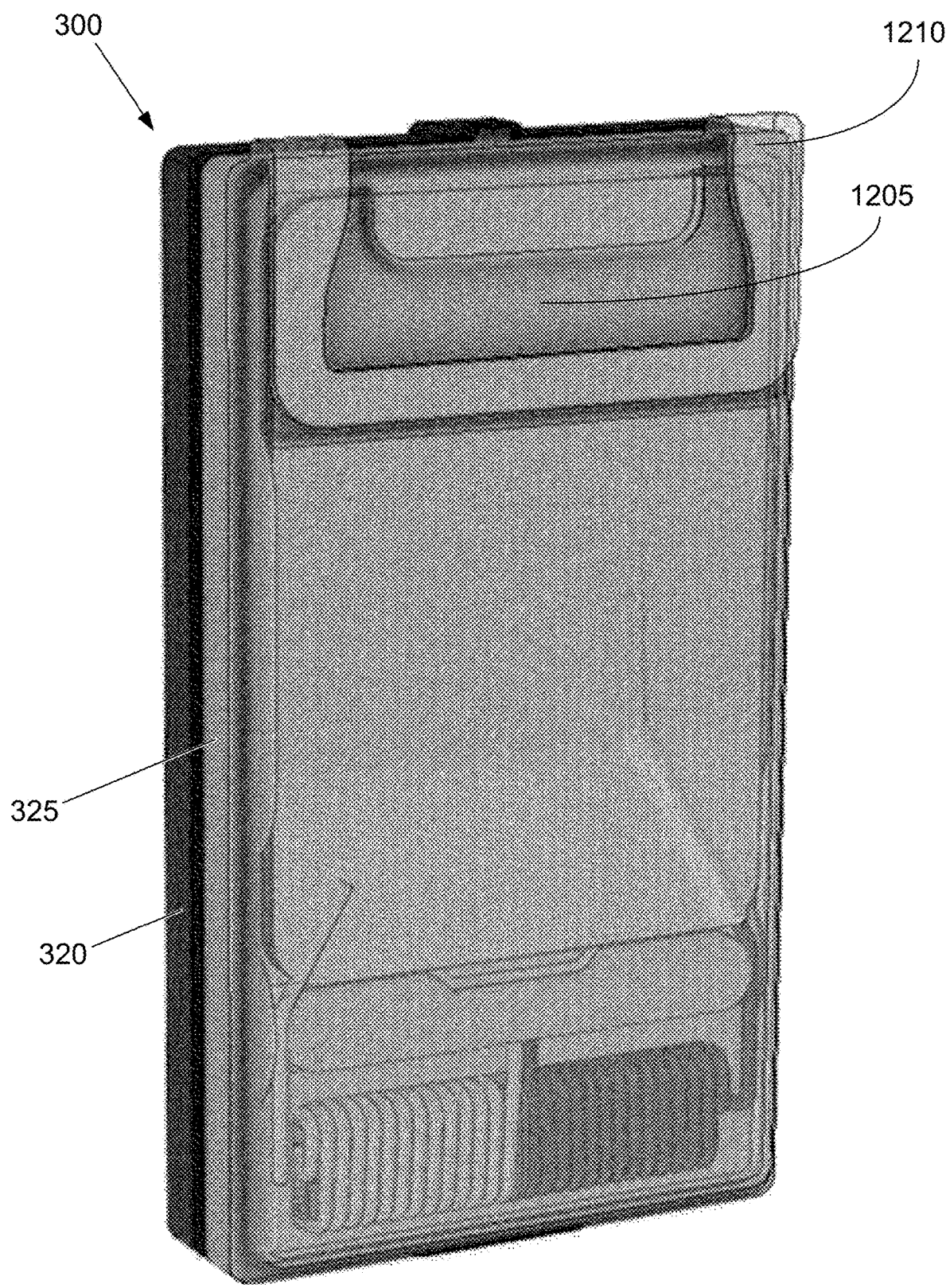
FIG. 12 is a rear perspective view of the medical device with the rear cover of the cartridge shown as transparent to enable viewing the AED electrode pads and coiled wires in storage.

As shown in FIG. 12, the cartridge (325) preferably has a rear cover (1210) with a handle (1205). FIG. 12 illustrates the rear cover (1210) shown as transparent to enable viewing the AED electrode pads and the coiled wires (1105) in storage. The rear cover (1210) would preferably not be transparent.

The handle (1205) may be used to remove the rear cover (1210). Once the rear cover (1210) is removed from the cartridge (325), the two AED electrode pads may simply fall out, or otherwise be removed, from their storage position within the cartridge (325) and the coiled wires (1105) connecting the two pins (430) to the AED electrode pads may be easily pulled off the end of the spool (1010) to extend the AED electrode pads for placement on the person (905). The two AED electrode pads are the first AED electrode pad (920) and the second AED electrode pad (925). Each of the coiled wires (1105) is typically at least one meter in length, as is suggested by the international standard ("Medical electrical equipment—Part 2-4: Particular requirements for the basic safety and essential performance of cardiac defibrillators," International Electrotechnical Commission (IEC) standard 60601.2.4). The center or internal volume of the spool (1010) may be used to store excess wire if its full length is not needed.

Figure 7:
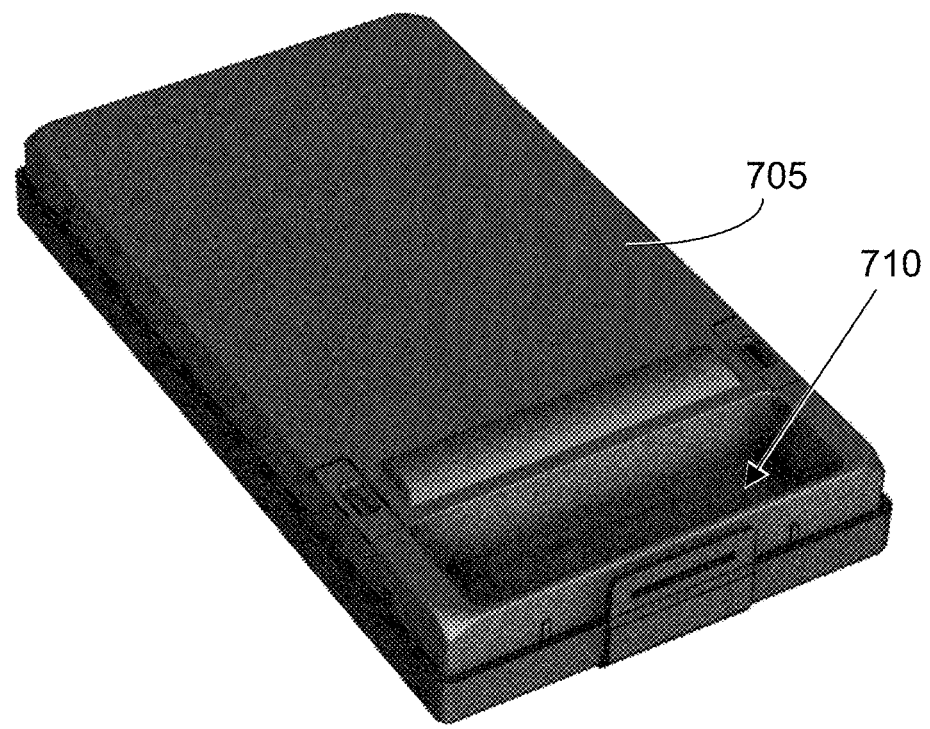
FIG. 7 is a perspective view of the rear of the AED body showing receptacles used to connect with pins on the cartridge to enable AED functionality and further showing a recess that would accommodate the coiled wires from the cartridge while in storage.

The AED (900) is made functional and ready to send an electrical charge through the pads when the relays disclosed above are activated, or if the cartridge (325) starts out separated from the AED body (320), then AED functionality begins when the two pins (430), also commonly known as spade lug terminals, or blades, extending from the cartridge (325) are plugged into the receptacles (805) in the AED body (320) and the relays are activated. FIG. 7 is a perspective view of the rear face (705) of the AED body (320) showing receptacles (805) used to connect with the two pins (430) on the cartridge (325) to enable the AED (900) to be functional and further showing a recess (710) that would accommodate the coiled wires (1105) from the cartridge (325) while in storage.

The Separating Step (205) is separating the medical device (300) into two components: a cartridge (325) and an AED body (320). Preferably, the Separating Step (205) is easily performed by disconnecting one or more snap-on clips. For example, there may be one snap-on clip at the top of the medical device (300) and/or one snap-on clip at the bottom of the medical device (300). The one or more snap-on clips may be used to connect and disconnect the cartridge (325) from the AED body (320).

Figure 14:
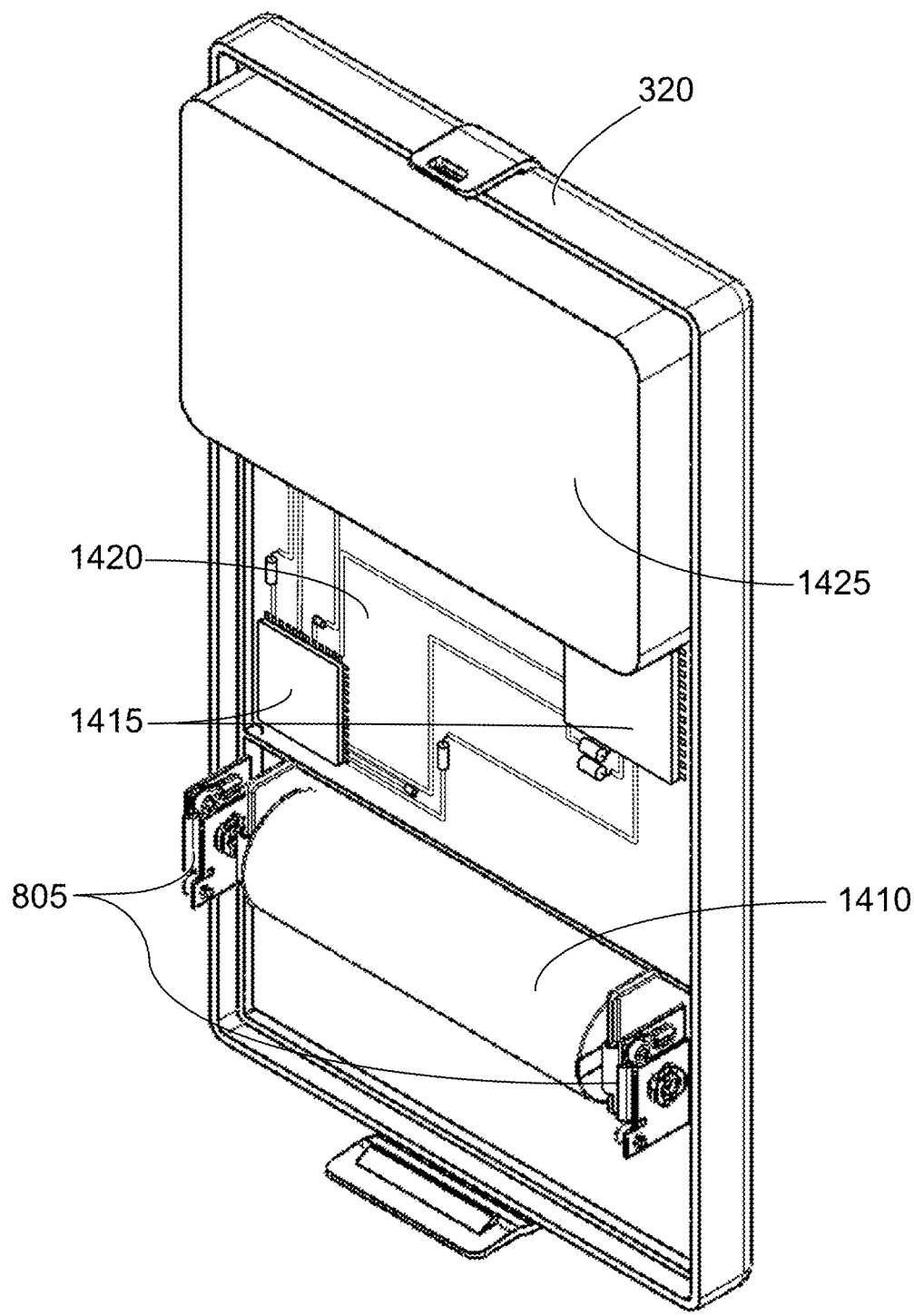
FIG. 14 is a rear perspective view of the AED body showing receptacles, battery, capacitor and a circuit board with CPUs within the AED body.
Figure 15:
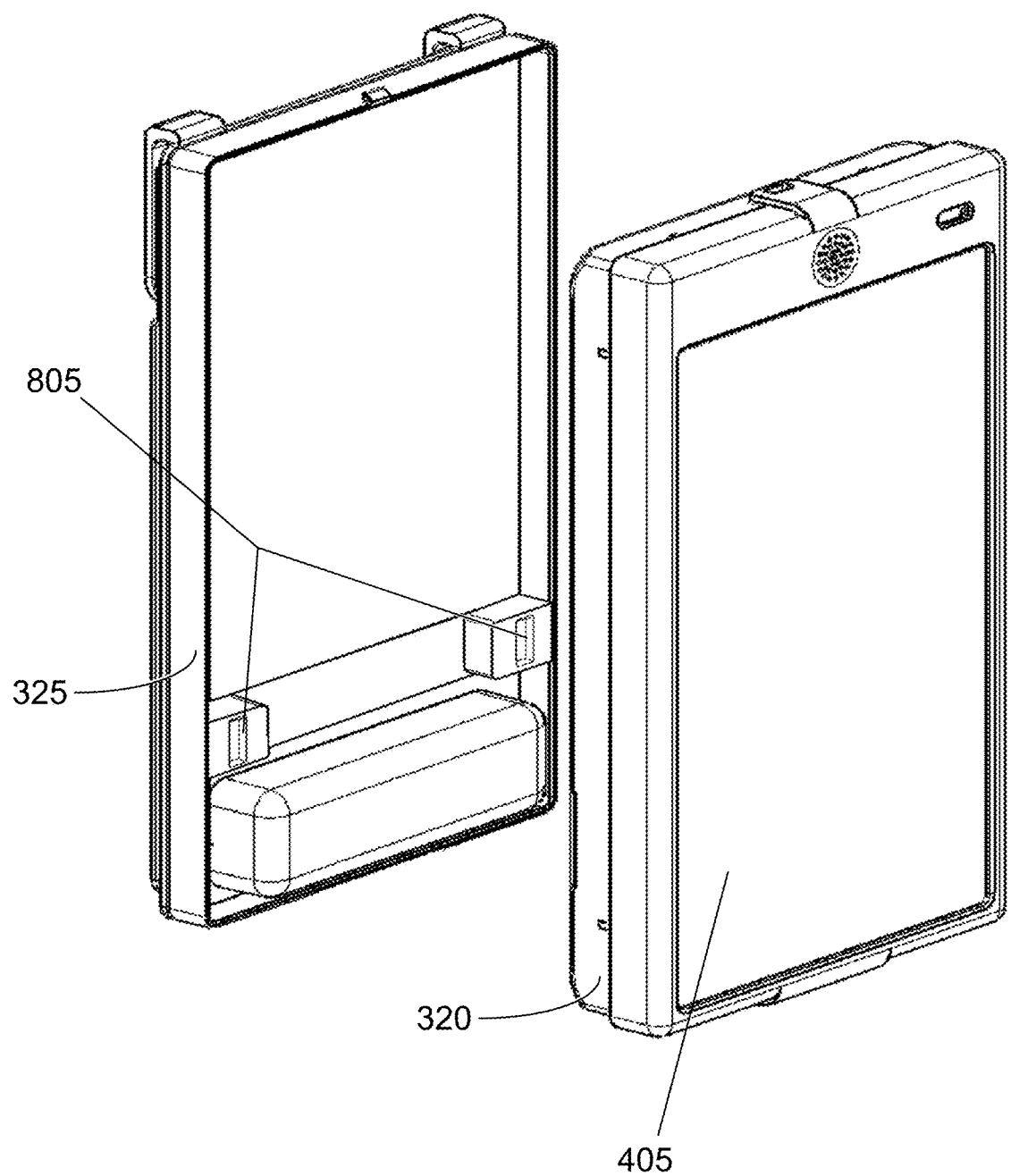
FIG. 15 is an exploded view of the medical device showing an alternative embodiment with receptacles on the cartridge and in position to receive the pins on the AED body.
Figure 16:
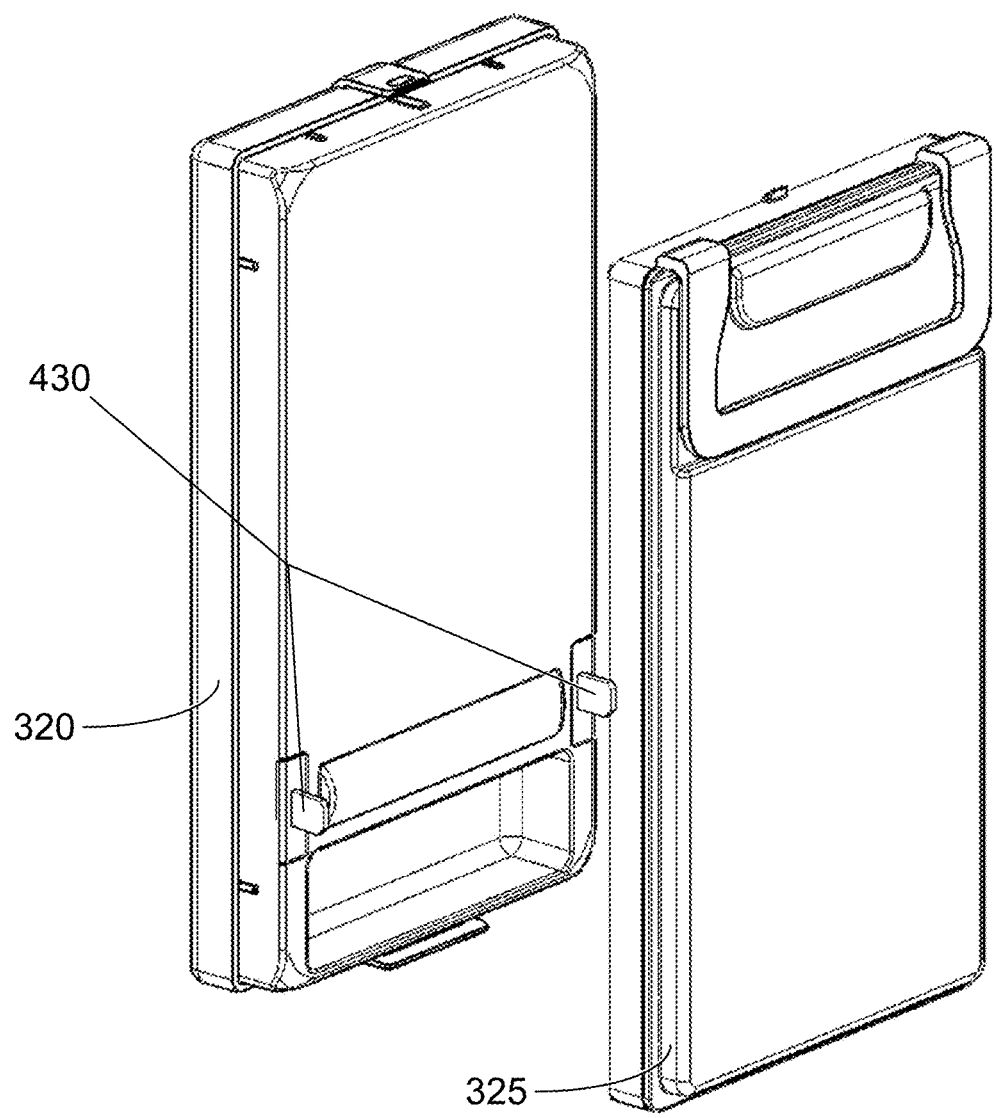
FIG. 16 is an exploded view of the medical device showing the alternative embodiment of FIG. 15 with the pins on the AED body in position for insertion into the receptacles on the cartridge.

The Plugging Step (210) is plugging the two pins (430) extending from the cartridge (325) into two of the receptacles (805) on the AED body (320). The receptacles (805) are capable of being switched on to electrically connect to a source of electricity, such as a battery (1410) or a capacitor (1425), shown in FIG. 14. This source of electricity is preferably self-contained within the AED body (320), but may alternatively be connected to an external electricity supply. In an alternative embodiment shown in FIG. 15 and FIG. 16, the two pins (430) and the receptacles (805) are exchanged in their position on the components of the medical device (300). This use of this alternative embodiment is explained in the Alternative Plugging Step (220).

The Alternative Plugging Step (220) is plugging the two pins (430) extending from the AED body (320) into the receptacles (805) on the cartridge (325). The two pins (430) are similarly capable of being automatically or manually switched on to electrically connect to the source of electricity. The two receptacles include: a first receptacle electrically connected to the first AED electrode pad (920), and a second receptacle electrically connected to the second AED electrode pad (925). The Alternative Plugging Step (220)

encompasses an embodiment where the receptacles (805) and the two pins (430) are located in positions on the opposing components. This alternative Plugging Step (220) accomplishes the same functions as in a preferred embodiment where the pins are on the cartridge (325) and the receptacles are on the AED body (320).

Joining together the cartridge (325) and the AED body (320) may be accomplished by plugging the two pins (430) protruding from the cartridge (325) into the receptacles (805) on the AED body (320) and snapping the cartridge (325) to the AED body (320).

Figure 8:
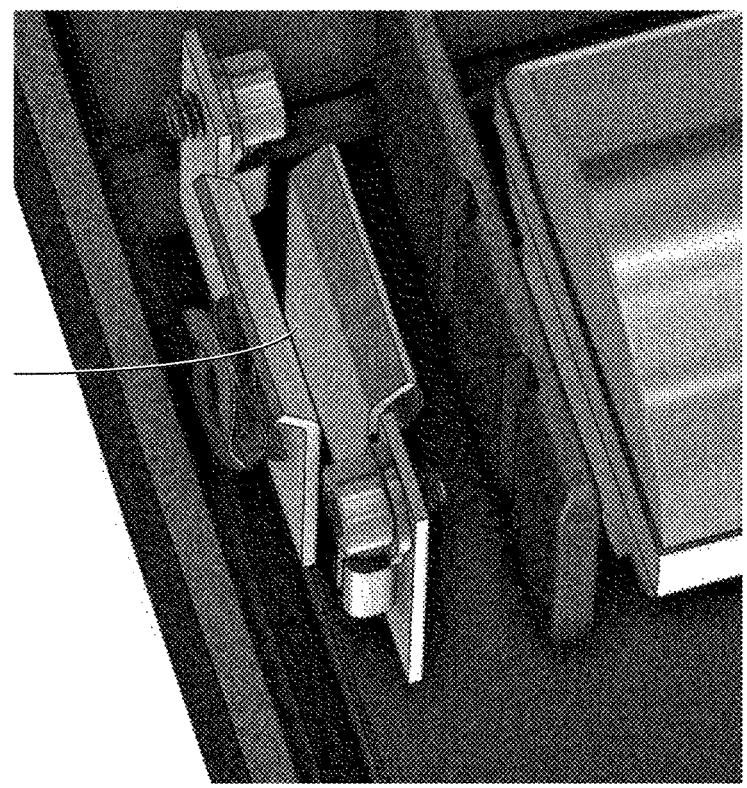
FIG. 8 is a close-in top perspective of a receptacle in the AED body used to connect to one of the two pins on the cartridge.

Preferably, each of the two receptacles (805) is a set of adjacent metal plates, as shown in FIG. 8. When inserted, each of the two pins (430) pushes the adjacent metal plates apart, ensuring good electrical contact. The adjacent metal plates provide a frictional fit that helps to remove any corrosion or foreign body buildup on the two pins (430). Preferably, when the two pins (430) are plugged into the two receptacles (805), this step also deactivates or switches off the first electrical contact (305) and the second electrical contact (310) of the medical device (300) when it also electrically connects the first AED electrode pad (920) and the second AED electrode pad (925).

Alternatively, the deactivation and switching off the electrical contacts is performed by a Switch Activating Step (215). The Switch Activating Step (215) is activating a switch that electrically disconnects the first electrical contact (305) and the second electrical contact (310) of the medical device (300) to the source of electricity and electrically connects the first AED electrode pad (920) and the second AED electrode pad (925) to the source of electricity. Activation preferably uses one or more switches and also preferably occurs electrically either automatically when the two pins (430) are plugged into the two receptacles (805) or manually.

The two pins (430) include a first pin (520R) electrically connected to the first AED electrode pad (920); and a second pin (520L) electrically connected to the second AED electrode pad (925). These two pins (430) within the cartridge (325) may be in two fixed positions extending outwardly from the cartridge (325). Alternatively, each of the two pins (430) may be hinged to fold down and collapse flat for storage.

Preferably, the two pins (430) project outwardly from the cartridge (325). As shown in FIG. 4, the two pins (430) are preferably located on opposite sides of the cartridge (325) to maximize electrical isolation of the first AED electrode pad (920) from the second AED electrode pad (925) once the two pins (430) are inserted into the receptacles (805) and connected to the source of electricity, which may be one or more of a battery (1410), a capacitor (1425), or an external electricity supply.

The two pins (430) preferably extend outwardly from the cartridge (325) in a configuration that provides an ability to be easily inserted into the receptacles (805). Plugging the cartridge (325) into the receptacles (805) and completing the transformation of the medical device (300) to the AED (900). Plugging in the cartridge (325) preferably connects the AED electrode pads to an internal source of electricity from the battery (1410) and the capacitor (1425). In some embodiments, energizing the AED electrode pads uses an external source of electricity is preferably also accomplished through the receptacles (805). Plugging the cartridge (325) into the receptacles (805) electrically connects the first AED electrode pad (920) and the second AED electrode pad (925) through the coiled wires (1105) to the source of electricity, which is preferably within the AED body (320), to enable functioning of the AED (900) to deliver an electric shock (915) to the person (905).

Each AED electrode pad is separately and individually connected by the separate and individual coiled wires (1105) to the two pins (430). In some embodiments, when the two pins (430) on the cartridge (325) are plugged into the receptacles (805) on the AED body (320), the AED electrode pads are then individually connected to a source of electricity, which is preferably a battery (1410) and/or a capacitor (1425) within the AED body (320). When more than two AED electrode pads are present, preferably, the same pins may be used to connect the additional AED electrode pads. Alternatively, the source of electricity may be an external supply connected to the AED body (320) through relays, transistors, switches or other electrical components that enable AED electrode pad connections and, which preferably electrically disconnect the first electrical contact (305) and the second electrical contact (310).

The Attaching Step (135) is attaching the first AED electrode pad (920) and the second AED electrode pad (925) to a person (905) to be treated with the AED (900). A typical placement of the AED electrode pads for an adult is illustrated in FIG. 9. Once the first AED electrode pad (920) and the second AED electrode pad (925) are deployed on a person (905) and used for defibrillation, the medical device (300) is preferably restored to its original capabilities by simply reattaching a new or replacement cartridge.

Finally, the Activating Step (140) is activating the AED body (320) to send an electrical charge between the first AED electrode pad (920) and the second AED electrode pad (925). The activation may happen manually or automatically.

The medical device (300) is preferably operable using a circuit board (1420) having two central processing units, or two CPUs (1415). Alternatively, two or more circuit boards may be used. This is referred to as a segmented processing architecture. Preferably, the medical device (300) has a unique architecture for the circuit board (1420) that allows the circuit board (1420) to fold over on itself, thereby minimizing required storage space. Flexible printed circuits are commercially available. An example of a flexible, foldable, control board is a single RIGID-FLEX PCB. Conceptually, there may be one circuit board, which has a flexible section. The foldable part of the circuit board (1420) is preferably a connector. It preferably has flexible "wires" in it which electrically connects two rigid pieces of the circuit board (1420). While flexible, the circuit board (1420) is preferably never "unfolded." The preferred design is that once the circuit board (1420) is installed in the AED body (320), the circuit board (1420) remains in a static position for the lifetime of the medical device (300).

A first of the two CPUs (1415) in the segmented processing architecture is configured to support cardiac rescues (the safety processor) using the AED (900). The safety processor preferably has no wireless communication capabilities.

The other of the two CPUs (1415) in the segmented processing architecture is configured for communication (the communication processor). For example, the communication processor may be used for, uploads or downloads of data via Wi-Fi or BLUETOOTH, or other cellular communications. This communications processor enables the BLUETOOTH, Wi-Fi and cellular capabilities. Wired, Wi-Fi, or BLUETOOTH communication may be used to communicate between device peripherals such as CPUs, AED electrode pads, or external electrical contacts.

Either of the two CPUs (1415) is operable if the other is turned off. Both CPUs (1415) can preferably interact when they are both on. Preferably, the two CPUs (1415) share a communications bus and power rails (power supplies). Each CPU has its own independent peripherals.

Alternatively, there may be two circuit boards. In that case, the two circuit boards would have a communications bus between them and would have independent power supplies.

The AED (900) lifesaving functionality and the ECG non-emergency diagnostic functions may share multiple internal components, which simplifies the design and reduces cost. The ECG capture and analysis hardware and firmware can be shared within the medical device (300). Only the electrical contacts and AED electrode pads preferably utilize different electrical paths for each operating mode.

The computer (335), which processes the ECG information for both filtering the ECG signal to reduce artifacts and then accurately evaluate the signal, is preferably used in both operating modes. Similarly, the communications hardware may be shared to send the information to external systems using protocols such as BLUETOOTH, Wi-Fi, or cellular.

Low-voltage power systems and battery charger systems are preferably shared by both modes, thus sharing a single battery, low voltage electrical circuitry, and charger interface.

The above-described embodiments including the drawings are examples of the invention and merely provide illustrations of the invention. Other embodiments will be obvious to those skilled in the art. Thus, the scope of the invention is determined by the appended claims and their legal equivalents rather than by the examples given.

INDUSTRIAL APPLICABILITY

The invention has application to the emergency medical industry.

What is claimed is:

1. A method of using a medical device, the method comprising the steps of:
   providing a medical device configured to:
      take one or more electrocardiograms (ECG);
      take the one or more ECG without deploying any AED electrode pad;
      take the one or more ECG using a first electrical contact and a second electrical contact that are accessible on an external surface of the medical device;
      require the first electrical contact and the second electrical contact to utilize a first electrical path that is different from a second electrical path utilized for any AED electrode pad;
      convert to a functional Automated External Defibrillator (AED), the functional AED configured to proved an electrical shock after using AED electrode pads to take the ECG to detect if a shockable arrythmia is present;
   identifying a need for the ECG from a person, the person having bare skin accessible to the medical device; and
   touching the bare skin to the first electrical contact and the second electrical contact of the medical device.

2. The method of claim 1, further comprising the step of reviewing the ECG on a computer.

3. The method of claim 1, wherein the person has a first hand with one or more fingers and has a second hand with one or more fingers, and wherein the step of touching the bare skin to the first electrical contact and the second electrical contact is accomplished by the person using a first finger from the first hand on the first electrical contact and a second finger from the second hand on the second electrical contact.

4. The method of claim 1, wherein the functional AED is further configured with:
   two AED electrode pad consisting of a first AED electrode pad and a second AED electrode pad;
   the method further comprising the steps of:
      removing the first AED electrode pad and the second AED electrode pad from a flattened and stacked arrangement within the medical device;
      attaching the first AED electrode pad and the second AED electrode pad to a person to be treated with the functional AED; and
      activating the AED body to send an electrical charge between the first AED electrode pad and the second AED electrode pad.

5. The method of claim 1, further comprising the step of:
   separating the medical device into two components, the two components comprising an AED body and a cartridge,
      the cartridge comprising a first AED electrode pad and a second AED electrode pad, the first AED electrode pad and the second AED electrode pad are electrically disconnected from a source of electricity when stored in the cartridge.

6. The method of claim 5, further comprising the steps of:
   removing the first AED electrode pad and the second AED electrode pad from a flattened and stacked arrangement within the cartridge;
   plugging two pins extending from the cartridge into two receptacles on the AED body, the two receptacles capable of being switched on to electrically connect to the source of electricity; the two pins comprising:
   a first pin electrically connected to the first AED electrode pad; and
   a second pin electrically connected to the second AED electrode pad; and
   attaching the first AED electrode pad and the second AED electrode pad to a person to be treated with the AED.

7. The method of claim 6, further comprising the steps of:
   activating a switch that electrically disconnects the first electrical contact and the second electrical contact of the medical device from a source of electricity and electrically connects the first AED electrode pad and the second AED electrode pad to the source of electricity; and
   activating the AED body to send an electrical charge between the first AED electrode pad and the second AED electrode pad.

8. The method of claim 5, further comprising the steps of:
   removing the first AED electrode pad and the second AED electrode pad from a flattened and stacked arrangement within the cartridge;
   plugging two pins extending from the AED body into two receptacles on the cartridge, the two pins capable of being switched on to electrically connect to the source of electricity; the two receptacles comprising:
   a first receptacle electrically connected to the first AED electrode pad; and
   a second receptacle electrically connected to the second AED electrode pad; and
   attaching the first AED electrode pad and the second AED electrode pad to a person to be treated with the AED.

* * * * *